United States Patent [19]

Pyret et al.

[11] Patent Number: 5,009,640

[45] Date of Patent: Apr. 23, 1991

[54] SLIP CAP FOR CANNULA USE

[75] Inventors: Thomas W. Pyret, Portage; James L. Gallagher, Oshtemo, both of Mich.

[73] Assignee: The Upjohn Company, Kalamazoo, Mich.

[21] Appl. No.: 300,278

[22] Filed: Jan. 19, 1989

[51] Int. Cl.[5] ...... A61M 5/00

[52] U.S. Cl. ...... 604/117; 604/192

[58] Field of Search ...... 604/54, 73, 117, 192, 604/263, 278

[56] References Cited

U.S. PATENT DOCUMENTS

| | | | |
|---|---|---|---|
| 600,449 | 3/1898 | Richardson . | |
| 1,436,707 | 11/1922 | Gaschke . | |
| 2,091,438 | 6/1936 | Epstein . | |
| 2,371,086 | 11/1941 | Watson et al. . | |
| 2,529,836 | 11/1950 | Darlington | 604/192 |
| 2,631,586 | 9/1955 | Reilly . | |
| 2,848,997 | 8/1958 | Miskel et al. . | |
| 2,908,609 | 10/1959 | Aterno et al. . | |
| 2,922,420 | 1/1960 | Cheng . | |
| 3,073,306 | 1/1963 | Linder . | |
| 3,073,307 | 1/1963 | Stevens . | |
| 3,234,945 | 2/1966 | Waldman et al. . | |
| 3,294,063 | 12/1966 | Brodrick . | |
| 3,368,557 | 2/1968 | Hassing et al. . | |
| 3,380,450 | 4/1968 | Adelberger | 604/192 X |
| 3,415,248 | 12/1968 | Scott . | |
| 3,434,473 | 3/1969 | Smith | 604/117 |
| 3,491,757 | 1/1970 | Arce . | |
| 3,575,160 | 4/1971 | Vass et al. . | |
| 3,756,235 | 9/1973 | Burke et al. . | |
| 3,825,003 | 7/1974 | Kruck . | |
| 3,865,236 | 2/1975 | Rycroft . | |
| 3,874,383 | 4/1975 | Glowacki . | |
| 3,877,464 | 4/1975 | Vermes . | |
| 3,882,866 | 5/1975 | Zackheim . | |
| 3,888,234 | 6/1975 | Clark . | |
| 3,889,673 | 6/1975 | Dovey et al. . | |
| 4,009,716 | 3/1977 | Cohen . | |
| 4,018,222 | 4/1977 | McAleer et al. | 604/197 X |
| 4,022,191 | 5/1977 | Jamshidi . | |
| 4,040,421 | 8/1977 | Young . | |
| 4,057,060 | 11/1977 | Roth . | |
| 4,281,658 | 8/1981 | Child . | |
| 4,300,545 | 11/1981 | Goodnow et al. . | |
| 4,303,069 | 12/1981 | Cohen . | |
| 4,308,859 | 1/1982 | Child . | |
| 4,346,714 | 8/1982 | Child . | |
| 4,359,044 | 11/1982 | Child . | |
| 4,430,080 | 2/1984 | Pasquini et al. . | |
| 4,453,930 | 6/1984 | Child . | |
| 4,453,935 | 6/1984 | Newton | 604/197 |
| 4,581,024 | 4/1986 | Swenson . | |
| 4,657,535 | 5/1987 | Nishimura et al. | 604/263 |
| 4,659,330 | 4/1987 | Nelson . | |
| 4,710,171 | 12/1987 | Rosenberg . | |
| 4,737,150 | 4/1988 | Baeumle et al. . | |
| 4,846,801 | 7/1989 | Okuda et al. | 604/218 |
| 4,846,811 | 7/1989 | Vanderhoof | 604/263 |
| 4,850,970 | 7/1989 | Sutherland | 604/117 |

FOREIGN PATENT DOCUMENTS

| | | | |
|---|---|---|---|
| 78000 | 8/1954 | Denmark | 604/117 |
| 1169935 | 1/1959 | France . | |

OTHER PUBLICATIONS

Journal of Dairy Science, vol. 69, No. 1, pp. 353–357 (1986).

*Primary Examiner*—C. Fred Rosenbaum
*Assistant Examiner*—Mark O. Polutta
*Attorney, Agent, or Firm*—Flynn, Thiel, Boutell & Tanis

[57] ABSTRACT

An applicator for administering a veterinary pharmacological composition comprises a container having a cannula extending therefrom and a two-piece cap for releasably covering the cannula. The cap has an internal seal for sealing the cannula against leakage and contamination. In one embodiment of the invention, a cylindrical skirt is provided on the tip cap and it extends axially inwardly toward the container. The skirt covers a portion of the axial length of the base cap and it is effective to prevent contact of the user's finger or thumb with the outer end portion of the cannula while the tip cap is being removed.

18 Claims, 1 Drawing Sheet

SLIP CAP FOR CANNULA USE

FIELD OF THE INVENTION

This invention relates to an applicator for administering a veterinary pharmacological composition. The applicator comprises a container, a cannula extending from the container and a two-piece cap for covering the cannula. The two pieces of the cap are removable from the cannula in selected order so that when the outer piece of the cap is removed, only a portion of the length of the cannula is exposed so that it can be inserted into the udder of an animal and when both the inner and outer pieces of the cap are removed, the entire length of the cannula is exposed so that it can be inserted into the animal's udder. The cap is provided with sealing means for sealing the cannula against leakage and contamination.

DESCRIPTION OF THE PRIOR ART

It is known to treat mastitis and/or other diseases of the udder by injecting into the udder of the animal being treated a veterinary pharmacological composition containing a veterinary medicine, for example, penicillin, effective for treating mastitis and/or other diseases of the udder.

The cannula used for injecting the veterinary pharmacological composition through a teat into the udder preferably has a smooth surface and it is made of a nonabrasive, physiologically inert, synthetic resin, such as polyethylene, so that the cannula will not abrade or irritate the animal's tissue.

The cannula should be sealed from the ambient air prior to use thereof in order to prevent leakage of the veterinary pharmacological composition and to prevent contamination thereof. Heretofore, it has been customary to use a slip-type cap which frictionally engages the external surface of the cannula. Slip-type caps are apt to slip off cannulas accidentally and they do not provide as tight a seal as is desired. The present invention provides an improved slip-type cap which is less likely to be accidentally separated from the cannula and which seals more tightly against the cannula.

Further, the veterinary pharmacological composition may need to be injected directly into the teat or, alternatively, directly into the udder of the animal. The present invention provides a two-piece slip cap for a cannula, which cap permits the cannula to be inserted only partially into the teat when one part of the cap has been removed and permits full insertion of the cannula into the animal's udder when both parts of the cap have been removed.

SUMMARY OF THE INVENTION

According to the invention, there is provided an applicator for administering a veterinary pharmacological composition, comprising a container having a cannula extending therefrom and adapted for dispensing the veterinary pharmacological composition into the teat or the udder of an animal undergoing treatment. A two-part, tubular, slip cap system or sheath is releasably connected to the cannula and covers substantially the entire length of same. When one part of the slip cap system has been removed, only the outer portion of the cannula is exposed so that the cannula can be inserted only part-way into the teat of the animal. When both parts of the slip cap system have been removed, the entire length of the cannula is exposed so that the entire length of the cannula can be inserted into the udder. The slip cap system has an internal seal structure for releasably sealingly engaging the outer surface of the cannula whereby to prevent leakage of the veterinary pharmacological composition from the cannula and to prevent contamination of the contents of the cannula and the container.

In a preferred embodiment of the invention, the cannula is made of relatively resiliently deformable, low density polyethylene having a density of from about 0.91 to about 0.94. At least the inner part or base cap of the slip cap system is made of high density polyethylene having a density of about 0.940 to about 0.965 and higher than the density of the low density polyethylene of which the cannula is made. The outer part or tip cap of the slip cap system is made of either high density polyethylene or low density polyethylene. The high density polyethylene used to make the base cap of the slip cap system has a higher strength and greater hardness and it is less easily resiliently deformable than the low density polyethylene of which the cannula is made. The outer part or tip cap of the slip cap system has an internal annular ring or ridge which has an interference fit with the external surface of the cannula. The outer part or tip cap of the slip cap system is press-fit on the axially outer end of the cannula so that the ring resiliently deforms and sealingly engages the external wall of the cannula, whereby to prevent leakage of material from the cannula and to prevent contamination of the cannula.

DESCRIPTION OF PREFERRED EMBODIMENTS

Figure 1:
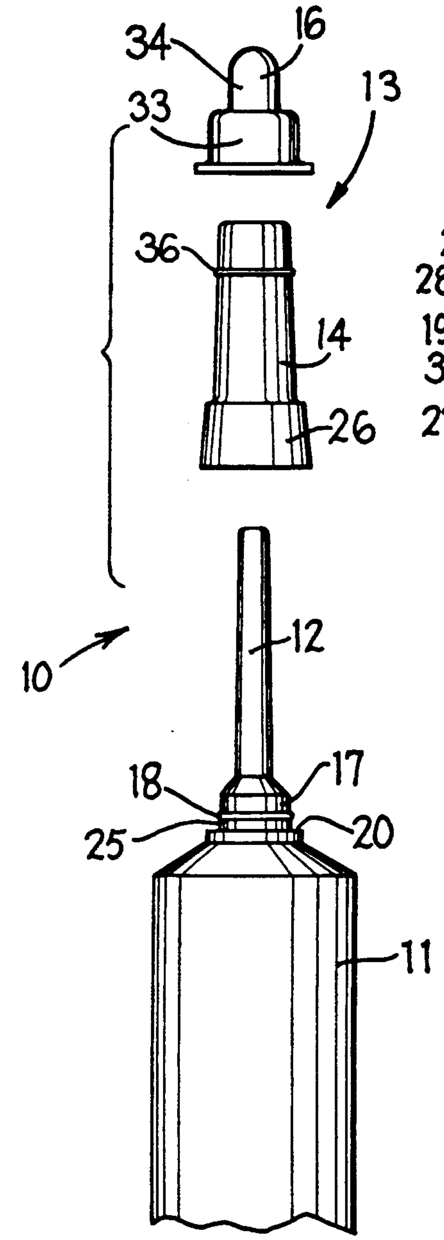
FIG. 1 is an exploded view of a container having a cannula and a two-part slip cap systems for the cannula, according to the invention.

Referring to FIG. 1, the applicator 10, according to the invention, generally comprises an elongated container 11 having a cannula 12 extending axially therefrom, and a two-part slip cap system or sheath 13 comprising a main body or base cap 14 and a tip cap 16.

The container 11 can be of any suitable type for parenteral administration of veterinary pharmacological compositions and it is of a size sufficient for holding the required dosage of the veterinary pharmaceutical composition. For example, the container 11 can be a sterile, disposable, hypodermic syringe barrel made of low density polyethylene. The container 11 has an integral, axially outwardly extending hub 17 at one end thereof. The hub 17 has a laterally outwardly projecting, annular rib 18 (FIGS. 1 and 2) on the external surface thereof, and has a central opening 19 extending longitudinally therethrough. The hub 17 has a flat wall 20 spaced downwardly a short distance from the rib 18 to define a groove 25 therewith. The opening 19 communicates with the interior chamber of the container 11. The cannula 12 extends axially from the hub 17 in a direction away from the container 11. The cannula 12 is an elongated, smooth-surfaced, tubular member and it has a central opening 21 extending lengthwise from the opening 19 in the hub 17. The opening 21 in the cannula is open at its longitudinally outer end. The longitudinally inner end of the opening 21 communicates with the opening 19 in the hub 17 and thence with the interior chamber of the container 11 so that the contents of the container can be dispensed through the cannula 12. The cannula 12 should be as long as is required for the deepest intended penetration into the udder of the animal to be treated. The cannula 12 preferably is slightly tapered in the longitudinally outward direction so that the external wall thereof extends at an angle of about 2° relative to the longitudinal axis of the cannula. This facilitates insertion and removal of the cannula.

The container 11, hub 17 and cannula 12 preferably are parts of a one-piece, monolithic, molded shape made of low-density polyethylene, as described in greater detail hereinbelow.

The main body or base cap 14 of the two-piece slip cap system 13 is generally cylindrical and elongated, and it has a laterally enlarged inner section 26 surrounding and releasably secured to the hub 17 of the container 11. Preferably, the main body 14 tapers in a direction away from the container 11. The enlarged inner section 26 of the main body 14 has an annular, laterally inwardly projecting ridge 27 at its longitudinally inner end and an end wall 30. An internal, annular, axially elongated groove 28 extends axially outwardly from adjacent to the ridge 27. When the main body 14 is releasably secured to the cannula 12, the end wall 30 of the main body 14 abuts against the flat wall 20 of the hub 17, the annular rib 18 on the hub 17 is received in the groove 28 and the ridge 27 underlies the rib 18 in order releasably to secure the main body 14 of the cap 13 to the hub 17 by a snap-lock effect. The axially outer end of the main body 14 of the cap 13 has a laterally inwardly extending shoulder 29 which defines an opening through which extends the axially outer end portion 31 of the cannula 12. The internal wall of the main body 14 is spaced from the external wall of the cannula 12, except at the ridge 27 and shoulder 29 so that these parts can be more easily flexed, relative to one another, as needed to effect removal of the cap.

Figure 3:
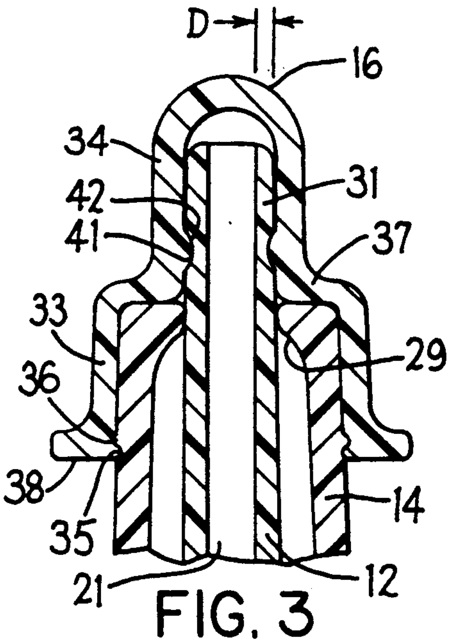
FIG. 3 is an enlarged view of the upper portion of FIG. 2.

The tip cap 16 has an axially inner tubular sleeve portion 33 which is sleeved on the axially outer portion of the main body 14 and an axially outer portion 34 of reduced diameter and which is sleeved on the axially outer end portion 31 of the cannula 12. The portion 34 is closed at its outer end and it covers the axially outer end portion 31 of the cannula 12. The inner surface of the sleeve portion 33 of the tip cap 16 is provided with an annular, laterally inwardly projecting, retaining ring 35 at its axially inner end for releasible engagement with the annular, laterally outwardly projecting, lock ring 36 on the main body 14 whereby the tip cap 16 is releasably engaged and held in place on the main body 14 of the cannula 12 by a snap-lock type of coupling. In this position, as shown in FIG. 3, the shoulder 37 of the tip cap 16, which shoulder extends laterally between the portions 31 and 34, abuts against the shoulder 29 on the main body 14 of the slip cap system 13.

A laterally outwardly projecting flange 38 is provided at the axially inner end of the tip cap 16. When the contents of the container 11 are to be dispensed, the user can manually engage the flange 38 with a finger or thumb and flip off the tip cap 16 from the main body 14, whereby the end portion 31 of the cannula becomes exposed and the contents of the container 11 can be dispensed. When the entirety of the slip cap system 13 is to be removed to expose the entire length of the cannula 12, the user can grasp the main body 14 and flex it to disengage the ridge 27 and rib 18 and then slide the entire slip cap system 13 axially off the cannula.

The inner surface of the axially outer portion 34 of the tip cap 16 has an annular, laterally inwardly projecting, sealing ring 41 which resiliently deforms the opposing portion of the external wall of the axially outer portion 31 of the cannula 12 whereby to form a complementary groove 42 therein. In this way, the ring 41 and groove 42 provide an effective, resilient seal between the tip cap 16 and the axially outward end portion 31 of the cannula 12. This serves to prevent leakage of the contents of the container 11 and to keep said contents sterile. For this purpose, the cannula 12 is preferably made of low density polyethylene having a density of from about 0.91 to about 0.94. The tip cap 16 is made of said low density polyethylene or high density polyethylene having a density of about 0.940 to about 0.965. Because high density polyethylene has a higher strength and hardness than the low density polyethylene, when the tip cap 16 is made of high density polyethylene and it is placed on the axially outer end of the cannula 12 and then is pushed axially inwardly therealong, the sealing ring 41 on the tip cap 16 will elastically deform successive portions of the external wall of the end portion 31 of the cannula 12 as it moves therepast until shoulder 37 abuts against shoulder 39. In that position, the ring 41 forms the groove 42 and the opposing wall portions of said ring and groove resiliently press against each other to form a tight seal between those parts and to hold the tip cap 16 in place. When the tip cap 16 is made of low density polyethylene, the ring 41 will be resiliently flattened more and the groove 42 will be less deep, but the opposing walls of the ring 41 and the groove 42 will still press against each other to form a tight seal between the tip cap 16 and the cannula 12.

In a typical environment of the invention, in which the external diameter of the axially outer end 31 of the cannula 12 is about 2.50 mm. and the wall thickness of the cannula is about 0.5 mm., the radial depth D of the sealing ring 41 is about 0.22 mm. In this example, the tip cap 16 is made either of high density polyethylene which is commercially available under the designation "MARTEX BMN TR800" or low density polyethylene, which is commercially available under the designation "Tenite 800A" and the cannula 12 is made of low density polyethylene which is commercially available under the designation "Tenite 800A". The main body 14 of the slip cap system 13 is made of high density polyethylene which is commercially available under the designation "Marlex BMNTR880".

When the tip cap 16 is secured to the outer end 31 of the cannula 12 and to the main body 14 of the slip cap system, the cannula 12 is protected from exposure and contamination and the entire applicator unit 10 can be safely stored and transported. When the pharmaceutical composition in the container 11 is to be administered, the tip cap 16 can be flipped-off by manually engaging the flange 38 whereby to expose the outer end portion 31 of the cannula. If a relatively shallow depth of penetration of the cannula 12 is desired, the outer end portion 31 of the cannula 12 can be inserted until the shoulder 29 abuts against the flesh of the animal. The shoulder 29 limits the depth of penetration of the cannula into the animal. When it is desired to expose a greater length of the cannula, then the main body 14 of the slip cap system can be removed by flexing and pulling said main body upwardly relative to the cannula 12. When the main body portion 14 is removed, then the entire length of the cannula 12 is exposed and the cannula can be inserted into the animal to the maximum extent.

MODIFICATION

Figure 2:
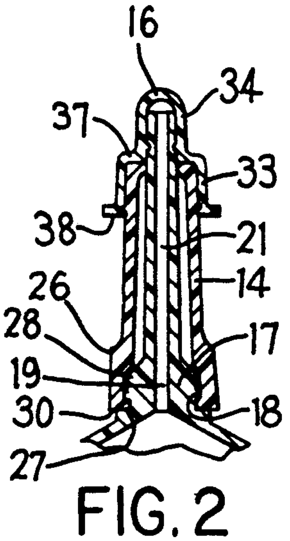
FIG. 2 is a central cross-sectional view of the cannula and slip cap of FIG. 1.
Figure 4:
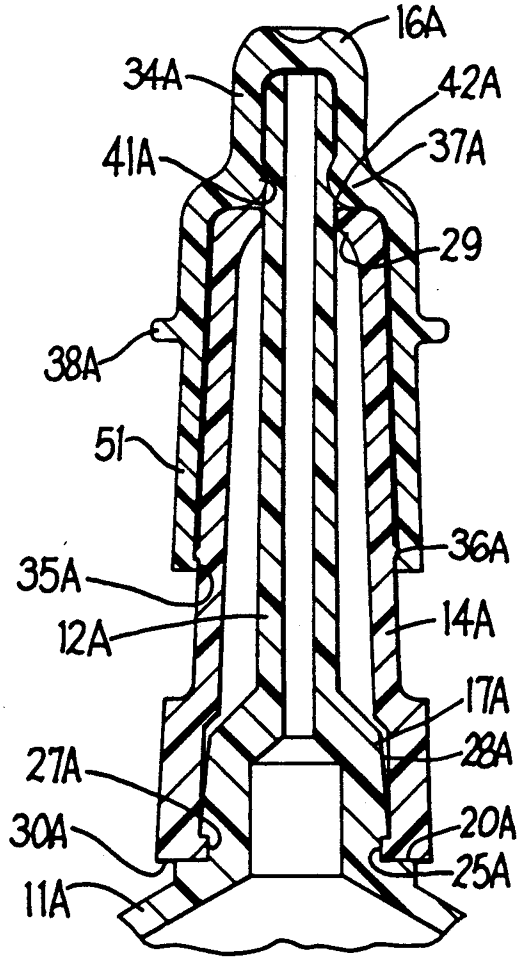
FIG. 4 is a view like FIG. 2 and showing a modification of the invention.

A modified slip cap system is shown in FIG. 4. The parts of this figure which correspond to parts in the embodiment of FIGS. 1 to 3 are identified by the same reference numbers with the suffix "a" applied thereto. This modification differs from the modification of FIGS. 1 through 3 by the provision of a cylindrical skirt 51 which extends downwardly from the flange 38*a* to cover a greater portion of the length of the main body portion 14*a* of the slip cap system. Also, the interengaging lock ring and sealing ring 35*a* and 36*a* are provided at the inner end of the tip cap 16*a*. Further, the ring 41*a* and complementary cavity 42*a* are provided substantially at the juncture of the shoulder 37*a* with the outer cap portion 34*a*. Also, the hub 17*a* flares in a direction toward the container 11, the rib 18 is omitted and the groove 25*a* is formed between the inner end of hub 17*a* and the shoulder 20*a*.

The applicator according to the invention protects the cannula from damage and contamination during storage, shipment and use. It permits the cannula to be inserted into the body of the animal to various depths, as needed for proper administration of the veterinary pharmaceutical composition. Because the end portion 31 and the remainder of the cannula 12 are completely covered by the tip cap 16 and the main body 14, respectively, the cannula is maintained in a sterile condition and is not exposed until the tip cap and/or main body are removed. Also, because the surfaces of shoulder 29 and hub 17, which are likely to contact the skin of the animal, are maintained in a sterile condition, there is a lower possibility of infection.

Although particular preferred embodiments have been illustrated and described, the invention contemplates such changes or modifications therein as lie within the scope of the appended claims.

The embodiments of the invention in which an exclusive property or privilege is claimed are defined as follows:

1. A device for administering a pharmacological composition, comprising: a container having an axially elongated, blunt-tipped cannula extending therefrom, said cannula having an axially inner portion and an axially outer portion; a two-part, tubular, tip cap system releasably connected to and covering said cannula, said tip cap system comprising an axially inner base cap and an axially outer tip cap, said base cap having an axially elongated tubular sidewall covering the axially inner portion of said cannula, said base cap having an outer end with an opening therethrough, the outer portion of said cannula extending through said opening and projecting outwardly beyond said outer end of said base cap, said tip cap having an axially inner, relatively wide, first sleeve portion and an axially outer, relatively narrow, second sleeve portion, said first sleeve portion being sleeved on the outer end of said base cap and being releasably secured thereto, said second sleeve portion being sleeved on and covering said outer portion of said cannula, a laterally inwardly projecting sealing ring on an inner surface of said second sleeve portion, said sealing ring being press fit on an exterior sidewall of said outer portion of said cannula and resiliently deforming the exterior sidewall of said outer portion of said cannula to form a complementary groove therein so that said sealing ring is in releasable sealing engagement with said exterior sidewall of said outer portion of said cannula in order to prevent leakage of fluid therebetween.

2. A device for treating diseases of the udder in cattle, comprising: a container for holding a supply of a veterinary pharmaceutical composition; an elongated, smooth-surfaced, blunt-tipped, tubular cannula extending from said container, said cannula being made of low density polyethylene having a density of from about 0.91 to about 0.94, said cannula having a hub portion of enlarged diameter at its axially inner end and joined to said container, said cannula having an axially inner end portion and an axially outer end portion, the axially outer end of said cannula being open and adapted for being received in the udder of an animal; a two-part, tubular, slip cap system sheathed on said cannula and covering the entire length thereof, said slip cap system having a tubular tip cap and a tubular base cap, said base cap being open at its opposite ends and covering a major portion of the length of said cannula, the axially outer end portion of said cannula projecting through and beyond the outer end of said base cap, a first snap-lock joint for releasably coupling the inner end of said base cap of said slip cap system to said hub portion of said cannula, said tip cap of said slip cap system having an open inner end and a closed outer end, the outer end of said base cap being longitudinally slidably received in the inner portion of the central opening of said tip cap, a second snap-lock joint for releasably connecting said tip cap to said base cap, the internal wall of the outer portion of said tip cap closely surrounding the axially outer end portion of said cannula and the closed outer end of said tip cap overlying the open end of said cannula, a sealing ring projecting laterally inwardly from said internal wall of the outer portion of said tip cap, said sealing ring being press fit on an external surface of the sidewall of said outer end portion of said cannula and resiliently deforming said external surface to form a complementary groove therein so that said sealing ring is in releasable sealing engagement with said external surface whereby to prevent leakage therebetween, said tip cap being made of low density polyethylene or high density polyethylene having a density in the range of from about 0.940 to about 0.965, said tip cap being removable from said base cap to expose only the outer end portion of said cannula, said base cap being removable from said hub to expose the entire length of said cannula.

3. The device of claim 2 in which said tip cap comprises an inner cylindrical portion of enlarged diameter sleeve on the outer portion of said base cap, an outer cylindrical portion of reduced diameter sleeved on said outer end portion of said cannula and a radially extending shoulder extending between the adjacent ends of said inner and outer cylindrical portions and abutting against the outer end of said base cap, said sealing ring having a smaller internal diameter than the external diameter of the outer end portion of said cannula so that said sealing ring resiliently deforms the external wall of the outer end portion of said cannula into conformity with the shape of said ring to provide a seal therebetween.

4. The device of claim 3 in which said sealing ring is located closer to said shoulder than to the outer end of said cannula.

5. The device of claim 3 in which said sealing ring is located substantially at said shoulder.

6. The device of claim 2 in which said tip cap has an outwardly extending flange located inwardly from the outer end of said base cap, said flange being manually engagable to remove said tip cap from said base cap.

7. The device of claim 2 in which said second snap-lock joint comprises a radially outwardly projecting first ridge on said base cap and a radially inwardly projecting second ridge on said tip cap, said first and second ridges having an interference fit with each other so that said tip cap is removed by elastic deformation thereof.

8. The device of claim 6 in which said second snap-lock joint is located directly radially inwardly from said flange.

9. The device of claim 6 in which said tip cap has a cylindrical skirt surrounding said base cap and extending inwardly from said flange toward said hub, said second snap-lock joint being located at the inner end of said tip cap.

10. An applicator for administering a mastitis treatment medication to a cow, comprising: a container having an axially elongated, blunt-tipped cannula extending therefrom, said cannula having an axially inner portion and an axially outer portion; a two-part tubular cap system releasably connected with respect to said cannula, the two parts of said cap system being adapted to be separated from each other to provide for selectable depth of penetration of said cannula into a teat canal of the cow, said tubular cap system comprising an axially inner base cap and an axially outer tip cap, said base cap covering the axially inner portion of the length of said cannula and having an outer end wall adapted to abut against the end of the teat of the cow, the axially outer portion of said cannula extending through said outer end wall of said base cap, said tip cap being releasably secured to said base cap and covering said outer portion of said cannula and an adjacent portion of said base cap, said tip cap having an axially inner sleeve portion and an axially outer sleeve portion, said outer sleeve portion being sleeved on and covering said outer portion of said cannula, said axially inner sleeve portion comprising a tubular section covering said adjacent portion of said base cap, a laterally outwardly projecting manually engageable member at an axially inner end of said tubular section so that said tip cap can be removed from said base cap by applying a pushing or pulling force on said manually engageable member, a cylindrical skirt extending axially inwardly from said member toward said container and covering a portion of the length of said base cap, said skirt having an internal wall which is laterally outwardly spaced from an external wall of said base cap to provide an annular clearance space therebetween, said member being engageable by a finger or thumb of a user of the applicator so that said tip cap can be displaced from said base cap to expose said outer portion of said cannula, said cylindrical skirt covering said portion of the length of said base cap so that the user's finger or thumb does not contact said base cap or said outer portion of said cannula while said tip cap is being removed.

11. An applicator as claimed in claim 10, including a snap-lock joint for releasably connecting said tip cap to said base, cap, said snap-lock joint being located adjacent to an axially inner end of said cylindrical skirt.

12. An applicator as claimed in claim 11 in which said snap-lock joint comprises a laterally inwardly extending annular lock ring at an axially inner end of said tip cap, and a cooperating sealing ring on the exterior surface of said base cap.

13. An applicator as claimed in claim 10 in which said manually engageable member is a laterally outwardly extending flange on an outer surface of said tip cap.

14. An applicator as claimed in claim 13, including a snap-lock joint for releasably connecting said tip cap to said base cap, said snap-lock joint being located adjacent to an axially inner end of said cylindrical skirt.

15. An applicator as claimed in claim 14 in which said tubular section comprises a first cylindrical portion extending outwardly from said flange and sleeved on said adjacent portion of said base cap, said outer sleeve portion is a second cylindrical portion of reduced diameter relative to said first cylindrical portion and sleeved on said outer portion of said cannula, and a radially extending shoulder extending between adjacent ends of said first and second cylindrical portions and abutting against an outer end of said base cap, a sealing ring projecting laterally inwardly from an internal wall of said second cylindrical portion of said tip cap at said shoulder, said annular sealing ring having a smaller internal diameter than the external diameter of the outer portion of said cannula so that said sealing ring resiliently deforms an external wall of the outer end portion of said cannula into conformity with the shape of said ring to provide a seal therebetween.

16. An applicator for administering a mastitis treatment medication to a cow, comprising: a syringe having an axially elongated, blunt-tipped cannula extending therefrom, said cannula having an axially inner portion and an axially outer portion; a two-part, tubular, cap system releasably connected to and covering said cannula, said cap system comprising an axially inner base cap and an axially outer tip cap, said base cap having an axially elongated sidewall covering the axially inner portion of said cannula, a snap-lock fitting at an axially inner end of said base cap for releasably securing said base cap with respect to said cannula, said base cap having an outer end with an opening therethrough, the axially outer portion of said cannula extending through said opening and projecting outwardly beyond said outer end of said base cap, said tip cap comprising an axially inner, relatively wide, first sleeve portion having an axially inner end and an axially outer end, a cylindrical skirt extending axially inwardly from the axially inner end of said first sleeve portion and surrounding said base cap for a portion of the length thereof, said skirt constituting an axial extension of said first sleeve portion, an axially outer, relatively narrow, second sleeve portion covering the axially outer portion of said cannula and a laterally extending shoulder extending between adjacent ends of said first and second sleeve portions and abutting against the outer end of said base cap, said second sleeve portion having an internal sealing ring projecting laterally inwardly from an internal wall of said second sleeve portion, said sealing ring being pressed into an exterior sidewall of said outer portion of said cannula and resiliently deforming the exterior sidewall of said outer portion of said cannula to form a complementary groove therein so that said sealing ring is in releasable sealing engagement with said groove in said exterior sidewall of said outer portion of said cannula in order to prevent leakage of fluid therebetween; a laterally outwardly projecting, manually engageable, annular flange at the juncture of said skirt and said first sleeve portion, said skirt and said first sleeve portion having internal walls laterally outwardly spaced from an external wall of said base cap to provide an annular clearance space therebetween extending from adjacent to an axially inner end of said skirt to said shoulder, said flange being engageable by a finger or thumb of a user of the applicator so that said tip cap can be displaced from said base cap to expose said outer portion of said cannula, said cylindrical skirt covering said portion of the length of said base cap so that the user's finger or thumb does not contact said base cap or said outer portion of said cannula while said tip cap is being removed whereby to reduce the possibility of contamination of said outer portion of said cannula; and a releasable snap lock connection between the axially inner end of said skirt and an opposing portion of said base cap.

17. An applicator for administering a mastitis treatment medication to a cow, comprising: a syringe having an axially elongated cannula extending therefrom, said cannula having an axially inner portion and an axially outer portion; a two-part, tubular, cap system releasably connected to and covering said cannula, said cap system comprising an axially inner base cap covering the axially inner portion of said cannula and an axially outer tip cap covering the axially outer portion of said cannula, said base cap being releasably secured with respect to said cannula, said tip cap comprising an axially inner first sleeve portion and an axially outer, second sleeve portion, said first sleeve portion comprising a manually engageable part and a cylindrical skirt extending axially inwardly from said part and surrounding said base cap for a portion of the length thereof, said second sleeve portion covering the axially outer portion of said cannula, said second sleeve portion having sealing means sealingly engaging said outer portion of said cannula in order to prevent leakage of fluid; an internal wall of said first sleeve portion being laterally outwardly spaced from an external wall of said base cap to provide an annular clearance space therebetween extending from adjacent to an axially inner end of said skirt to an axially outer end of said first sleeve portion, said part being manually engageable sot hat said tip cap can be pushed or pulled axially to disengage said tip cap from said base cap to expose said outer portion of said cannula, said cylindrical skirt covering said portion of the length of said base cap so that the user's finger or thumb does not contact said base cap or said outer portion of said cannula while said tip cap is being removed whereby to reduce the possibility of contamination of said outer portion of said cannula.

18. An applicator as claimed in claim 18, including a releasable snap lock connection between the axially inner end of said skirt and an opening portion of said base cap.

* * * * *

UNITED STATES PATENT AND TRADEMARK OFFICE

CERTIFICATE OF CORRECTION

PATENT NO. : 5 009 640

DATED : April 23, 1991

INVENTOR(S) : Thomas W. Pyret et al

It is certified that error appears in the above-identified patent and that said Letters Patent is hereby corrected as shown below:

Column 4, line 46; change "TR800" to ---TR-880---.

Column 10, line 14; change "sot hat" to ---so that---.

Column 10, line 24; change "claim 18," to ---claim 17,---.

Column 10, line 26; change "opening" to ---opposing---.

Signed and Sealed this

Sixteenth Day of March, 1993

*Attest:*

STEPHEN G. KUNIN

*Attesting Officer*

*Acting Commissioner of Patents and Trademarks*